United States Patent

Sirhan et al.

[11] Patent Number: 6,013,069
[45] Date of Patent: Jan. 11, 2000

[54] CATHETER SHAFT WITH AN OBLONG TRANSVERSE CROSS-SECTION

[75] Inventors: Motasim M. Sirhan, Sunnyvale; Jovito L. Fernando, Sr., Modesto; Troy L. Thornton, San Francisco, all of Calif.; Patrick K. Campbell, Georgetown, Mass.; Eric Williams, Fairfield; Lawrence D. Wasicek, Sunnyvale, both of Calif.

[73] Assignee: Advanced Cardiovascular Systems, Inc., Santa Clara, Calif.

[21] Appl. No.: 09/063,874

[22] Filed: Apr. 21, 1998

Related U.S. Application Data

[63] Continuation of application No. 08/742,689, Nov. 4, 1996, Pat. No. 5,743,875, which is a continuation of application No. 08/368,794, Jan. 4, 1995, abandoned, which is a continuation-in-part of application No. 08/250,708, May 27, 1994, abandoned, which is a continuation-in-part of application No. 08/021,062, Apr. 15, 1993, abandoned, which is a continuation-in-part of application No. 08/192,065, Feb. 4, 1994, Pat. No. 5,496,275, which is a continuation of application No. 08/095,814, Jul. 20, 1993, which is a continuation-in-part of application No. 07/700,617, May 15, 1991, and a continuation-in-part of application No. 07/870,820, Apr. 20, 1992, abandoned.

[51] Int. Cl.⁷ ............................................. A61M 29/00
[52] U.S. Cl. ......................... 604/524; 604/96; 604/194
[58] Field of Search ..................... 604/95, 96, 264, 604/200, 202

[56] References Cited

U.S. PATENT DOCUMENTS

| | | | |
|---|---|---|---|
| 2,248,934 | 7/1941 | Auzin | 604/103 |
| 2,457,244 | 12/1948 | Lamson | 604/96 |
| 2,912,981 | 11/1959 | Keough | 604/98 |
| 2,930,377 | 3/1960 | Cowley | 128/344 |
| 3,112,748 | 12/1963 | Colburn | 128/350 R |
| 3,769,981 | 11/1973 | McWhorter | 604/96 |
| 3,915,171 | 10/1975 | Shermeta | 128/348 |
| 3,978,863 | 9/1976 | Fettel et al. | 604/192 |
| 3,983,879 | 10/1976 | Todd | 604/96 |
| 4,295,464 | 10/1981 | Sihata | 604/98 |
| 4,406,656 | 9/1983 | Hattler et al. | 604/43 |
| 4,458,677 | 7/1984 | McCorkle, Jr. | 128/786 |

(List continued on next page.)

FOREIGN PATENT DOCUMENTS

| | | |
|---|---|---|
| 197787 | 10/1986 | European Pat. Off. . |
| 0 274 129 | 7/1988 | European Pat. Off. . |
| 0374859 | 6/1990 | European Pat. Off. . |
| 0 397 055 | 11/1990 | European Pat. Off. . |
| 0441384 | 8/1991 | European Pat. Off. . |
| 0 491 349 | 6/1992 | European Pat. Off. . |
| 0 513 818 | 11/1992 | European Pat. Off. . |
| 3522782 A1 | 1/1987 | Germany ............ 604/44 |
| 3742710 | 7/1989 | Germany ........... 604/280 |
| WO 93/18813 | 9/1993 | Japan . |
| WO 93 20882 | 10/1993 | WIPO . |

*Primary Examiner*—Corrine McDermott
*Assistant Examiner*—Kent Gring
*Attorney, Agent, or Firm*—Heller, Ehrman, White & McAuliffe

[57] ABSTRACT

A balloon dilatation catheter having a catheter shaft with an oblong transverse cross-section with one transverse dimension in a first direction being significantly larger than a second transverse dimension in a direction perpendicular to the first direction. The first dimension is about 1.1 to about 3 times greater, preferably about 1.2 to about 2.5 times greater than the second dimension. In one embodiment, a length of the distal shaft section has inner and outer tubular members where about 30% to not more than about 90% of the inner periphery of the outer tubular member takes the shape of and is secured to the exterior of the inner tubular member. In another embodiment the flexible distal shaft section is an extruded section having an oval or elliptical transverse cross-section. Preferably a pseudoelastic hypotube of NiTi alloy defines at least part of the inflation lumen within the catheter shaft. In another embodiment of the invention the proximal shaft of the catheter has an inner and outer tubular member.

20 Claims, 6 Drawing Sheets

U.S. PATENT DOCUMENTS

| | | | |
|---|---|---|---|
| 4,484,579 | 11/1984 | Meno et al. | 606/194 |
| 4,553,959 | 11/1985 | Hickey et al. | 604/96 |
| 4,563,170 | 1/1986 | Aigner . | |
| 4,601,713 | 7/1986 | Fuqua | 604/96 |
| 4,723,936 | 2/1988 | Buchbinder et al. | 604/96 |
| 4,748,982 | 6/1988 | Horzewski | 606/192 |
| 4,771,777 | 9/1988 | Horzewski et al. | 604/96 |
| 4,776,841 | 10/1988 | Catalano | 604/280 |
| 4,790,315 | 12/1988 | Mueller, Jr. et al. | 606/194 |
| 4,850,373 | 7/1989 | Zatloukal et al. . | |
| 4,877,031 | 10/1989 | Conway et al. | 604/96 |
| 4,892,519 | 1/1990 | Songer et al. | 604/96 |
| 4,906,230 | 3/1990 | Moloney et al. | 604/95 |
| 4,917,666 | 4/1990 | Solar et al. | 604/96 |
| 4,943,278 | 7/1990 | Euteneuer et al. | 606/194 |
| 4,944,745 | 7/1990 | Sogard et al. | 604/103 |
| 4,998,923 | 3/1991 | Samson et al. | 604/95 |
| 5,037,386 | 8/1991 | Marcus et al. | 604/43 |
| 5,040,548 | 8/1991 | Yock | 128/898 |
| 5,046,503 | 9/1991 | Schneiderman | 606/194 |
| 5,071,425 | 12/1991 | Gifford, III et al. | 606/159 |
| 5,102,390 | 4/1992 | Crittenden et al. | 606/194 |
| 5,106,368 | 4/1992 | Uldall et al. | 604/43 |
| 5,135,535 | 8/1992 | Kramer | 606/194 |
| 5,149,330 | 9/1992 | Brightbill | 604/280 |
| 5,154,725 | 10/1992 | Leopold | 606/194 |
| 5,156,594 | 10/1992 | Keith | 604/96 |
| 5,171,222 | 12/1992 | Euteneuer et al. | 604/102 |
| 5,195,971 | 3/1993 | Sirhan | 604/96 |
| 5,217,440 | 6/1993 | Frassica | 604/282 |
| 5,279,562 | 1/1994 | Sirhan et al. | 604/96 |
| 5,300,025 | 4/1994 | Wantink | 604/282 |
| 5,370,616 | 12/1994 | Keith et al. | 604/282 |
| 5,795,325 | 8/1998 | Valley et al. | 604/53 |

CATHETER SHAFT WITH AN OBLONG TRANSVERSE CROSS-SECTION

RELATED APPLICATIONS

This is a continuation application of copending application Ser. No. 08/742,689 filed on Nov. 4, 1996 now U.S. Pat. No. 5,743,845 which is a continuation of Ser. No. 08/368, 794 now abandoned filed Jan. 4, 1995 which is a CIP of Ser. No. 08/250,708 filed May 27, 1994 now abandoned which is a CIP of Ser. No, 08/021,062 filed Apr. 15, 1993 now abandoned and a CIP of Ser. No. 08/192,065 filed Feb. 4, 1994 now U.S. Pat. No. 5,496,275 which is a continuation of Ser. No. 08/095,814 filed Jul. 20, 1993 which is a CIP of Ser. No. 07/700,617 filed May 15, 1991 and CIP of Ser. No. 07/870,820 filed Apr. 20, 1992 now abandoned.

This application is a continuation-in-part of copending application Ser. No. 08/250,708, filed on May 27, 1994, which is a continuation-in-part of copending applications Ser. No. 08/021,062, filed on Apr. 15, 1993, and Ser. No. 08/192,065, filed on Feb. 4, 1994, the latter application being a continuation of Ser. No. 08/095,814, filed on Jul. 20, 1993, entitled LOW PROFILE DILATION CATHETER, which is a continuation-in-part of Ser. No. 07/700,617, filed on May 5, 1991, entitled LOW PROFILE DILATION CATHETER, and is a continuation-in-part of Ser. No. 07/870,820, filed on Apr. 20, 1992, entitled LOW PROFILE DILATION CATHETER.

BACKGROUND OF THE INVENTION

This invention generally relates to intravascular catheters, such as balloon dilatation catheters used in percutaneous transluminal coronary angioplasty (PTCA).

PTCA is a widely used procedure for the treatment of coronary heart disease wherein a balloon dilatation catheter is advanced into the patient's coronary artery and the balloon on the distal portion of the catheter is inflated within the stenotic region of the patient's artery to open up the arterial passageway and thereby increase the blood flow therethrough. To facilitate the advancement of the dilatation catheter into the patient's coronary artery, a guiding catheter having a preshaped distal tip is first percutaneously introduced into the cardiovascular system of a patient by the Seldinger technique through the brachial or femoral arteries and is advanced therein until the preshaped distal tip of the guiding catheter is disposed within the aorta adjacent the ostium of the desired coronary artery. The guiding catheter is twisted or torqued from its proximal end, which extends out of the patient, to guide the distal tip of the guiding catheter into the desired ostium. A balloon dilatation catheter may then be advanced through the inner lumen of the guiding catheter into the patient's coronary artery until the balloon an the dilatation catheter is disposed within the stenotic region of the patient's artery. The balloon is inflated and deflated one or more times to open up the arterial passageway and increase the flow of blood.

One type of catheter frequently used in PTCA procedures is an over-the-wire type balloon dilatation catheter. Commercially available over-the-wire type dilatation catheters include the SIMPSON ULTRA LOW PROFILE (TM), the HARTZLER ACX (R), the HARTZLER ACX II (TM), the PINKERTON 0.018 (TM) and the ACS TEN (TM) balloon dilatation catheters sold by the assignee of the present invention, Advanced Cardiovascular Systems, Inc. (ACS).

Another type of over-the-wire dilatation catheter is the rapid exchange type catheter, which was introduced by ACS under the trademark ACS RX® Coronary Dilatation Catheter. It is described and claimed in U.S. Pat. No. 5,040,548 (Yock), U.S. Pat. No. 5,061,273 (Yock), U.S. Pat. No. 4,748,982 (Horzewski et al.) and U.S. Pat. No. 5,154,725 (Leopold) which are incorporated herein by reference. This dilatation catheter has a short guidewire receiving sleeve or inner lumen extending through a distal portion of the catheter. The sleeve or inner lumen extends proximally from a first guidewire port in the distal end of the catheter to a second guidewire port in the catheter spaced proximally from the inflatable member of the catheter. A slit may be provided in the wall of the catheter body which extends distally from the second guidewire port, preferably to a location proximal to the proximal end of the inflatable balloon. The structure of the catheter allows for the rapid exchange of the catheter without the need for an exchange wire or adding a guidewire extension to the proximal end of the guidewire.

Some over-the-wire and rapid exchange type dilatation catheters have perfusion capabilities where one or more perfusion ports are provided in the catheter shaft proximal to the dilatation balloon which are in fluid communication with a guidewire receiving inner lumen extending to the distal end of the catheter. Additionally, one or more perfusion ports are preferably provided in the catheter shaft, distal to the balloon which are also in fluid communication with the guidewire receiving inner lumen. When the balloon of a dilatation catheter with perfusion capabilities is inflated to dilate a stenosis, oxygenated blood in the artery or the aorta or both, depending upon the location of the proximal perfusion parts of the dilatation catheter within the coronary anatomy, is forced to pass through the proximal perfusion ports, through the guidewire receiving inner lumen of the catheter and out the distal perfusion ports. The flow of oxygenated blood downstream from the inflated balloon minimizes ischemic conditions in tissue distal to the balloon and allows for long term dilatations, e.g. 30 minutes or even several hours or more. Commercially available perfusion type dilatation catheters include the STACK PERFUSION (TM) and the ACS RX PERFUSION (TM) dilatation catheters which are sold by ACS.

A continual effort has been made in the development of intravascular catheters, particularly angioplasty catheters, to reduce the transverse dimensions or profile of such catheters and the flexibility without detrimentally affecting the pushability and other characteristics of the catheters, particularly in the distal portion of the catheters which are advanced through tortuous anatomy. A balloon dilatation catheter with an increased flexibility and an increased pushability allow the catheter to be advanced much further into a patient's vasculature and to cross much tighter lesions.

Despite the many technical advances in these areas, the need for intravascular catheters having even greater flexibility and pushability remains. The present invention satisfies these and other needs.

SUMMARY OF THE INVENTION

The present invention is directed to an elongated intravascular catheter with improved flexibility and pushability, particularly in the distal portion thereof.

The catheter shaft of the invention has, at least in the distal portion thereof, an oblong transverse cross-section wherein the transverse dimension in a first direction is larger than the transverse dimension in a second direction perpendicular to the first direction. In a presently preferred embodiment the larger transverse dimension is about 1.1 to about 3 times, preferably about 1.2 to about 2.5 times, greater than the smaller perpendicular transverse dimension. For dilatation catheters suitable for coronary arteries the differential between the first and second transverse dimensions is at least about 0.003 inch (0.076 mm) and for dilatation catheters for peripheral use this differential should be at least about 0.005 inch (0.127 mm). The shape of the oblong transverse cross-section proximal to the balloon is preferably oviform or elliptical in nature. The length of the oblong portion of the catheter shaft is at least about 4 cm., preferably at least about 7 cm. The entire length of the catheter shaft may have the desired oblong transverse cross-section or only the portion of the catheter which extends out of the guiding catheter, e.g. about 10 to about 40 cm. Advantages have also been recognized with the proximal portion of the catheter shaft having an oblong transverse cross-section in accordance with this invention.

In one embodiment the intravascular catheter of the invention generally includes, at least in the distal portion thereof, an inner tubular member having an inner lumen extending therein and an outer tubular member disposed about the inner tubular member with at least about 30% and not more than about 90%, preferably not more than about 80%, of the inner periphery of the outer tubular member taking the shape of and being secured to exterior of the inner tubular member along a length of the catheter shaft of at least about 4 cm, preferably at least about 7 cm. An inner inflation lumen extends along the secured length between the portion of the outer tubular member which does not take the shape of and which is not secured to the underlying inner tubular member. The bond between the secured inner and outer tubular member need not be continuous. It may be intermittent, so long as a significant portion of the interface between the two members is secured along the length. The inner and outer tubular members may be secured together by heat or laser bonding, adhesive bonding, heat shrinking the outer tube onto the inner tube or other suitable means.

By securing a length of the outer tubular member in the distal portion of the catheter to the exterior of the inner member, the profile of the catheter body in at least one transverse dimension in that area is reduced substantially to thereby provide improved flexibility. Moreover, the secured portions of the inner tubular member and the outer tubular member support one another thereby providing improved pushability. Substantial reductions in only one transverse dimension can provide substantial improvements in flexibility. Minimum cross-sectional dimensions of the small diameter section of the outer tubular member for coronary dilatation catheters are on the order of about 0.01 to about 0.06 inch (0.51–1.5 mm). For peripheral arteries this dimension may be larger.

The improvements of the invention are applicable to a wide range of elongated intravascular catheters which are at least 90 cm in length and which are percutaneously introduced and advanced deep within the patient's vascular system, such as in the coronary anatomy. It is particularly suitable in essentially all types of dilatation catheters with inflatable or expandable dilatation members on their distal extremities, such as those described in the patents incorporated herein by reference. These and other advantages of the invention will become more apparent from the following detailed description of the invention when taken in conjunction with accompanying exemplary drawings.

DETAILED DESCRIPTION OF THE INVENTION

FIGS. 1–5 schematically illustrate an over-the-wire dilatation catheter 10 embodying features of the invention. The catheter 10 includes an elongated catheter shaft 11 which has an inner tubular member 12, an outer tubular member 13 disposed about the inner tubular member and an adapter 14 secured to the proximal ends of the inner and outer tubular members. A relatively inelastic, inflatable balloon 15 which is integral with the outer tubular member 13 and a distal skirt 17 which is secured to the distal end of the inner tubular member 12. Alternatively, the balloon 15 may be formed from different material and be secured to the outer tubular member 13.

Figure 1:
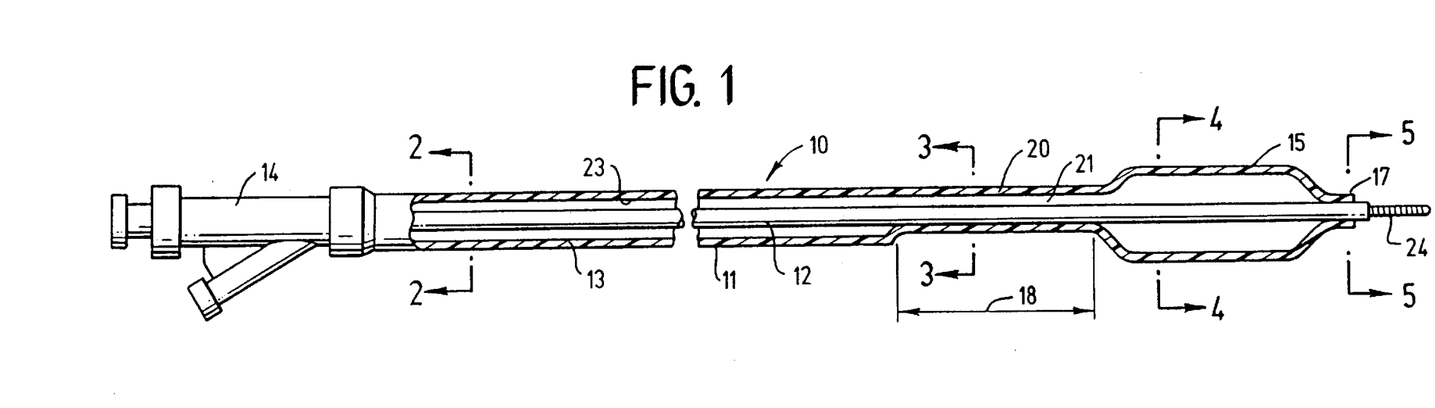
FIG. 1 is an elevational view, partially in section, of a balloon dilatation catheter embodying features of the invention.
Figures 3, 4:
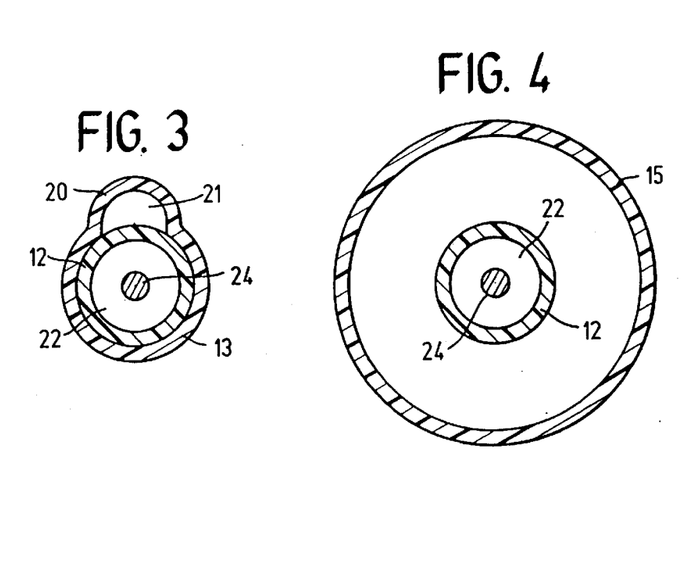
FIG. 3 is a transverse cross-sectional view of the catheter shown in FIG. 1 taken along the lines 3—3.
FIG. 4 is a transverse cross-sectional view of the catheter shown in FIG. 1 taken along the lines 4—4.
Figure 5:
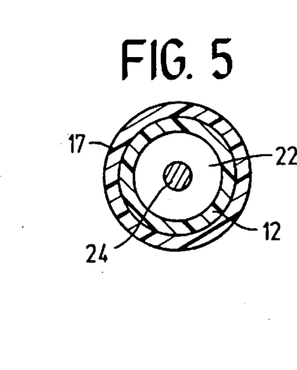
FIG. 5 is a transverse cross-sectional view of the catheter shown in FIG. 1 taken along the lines 5—5.
Figure 6:
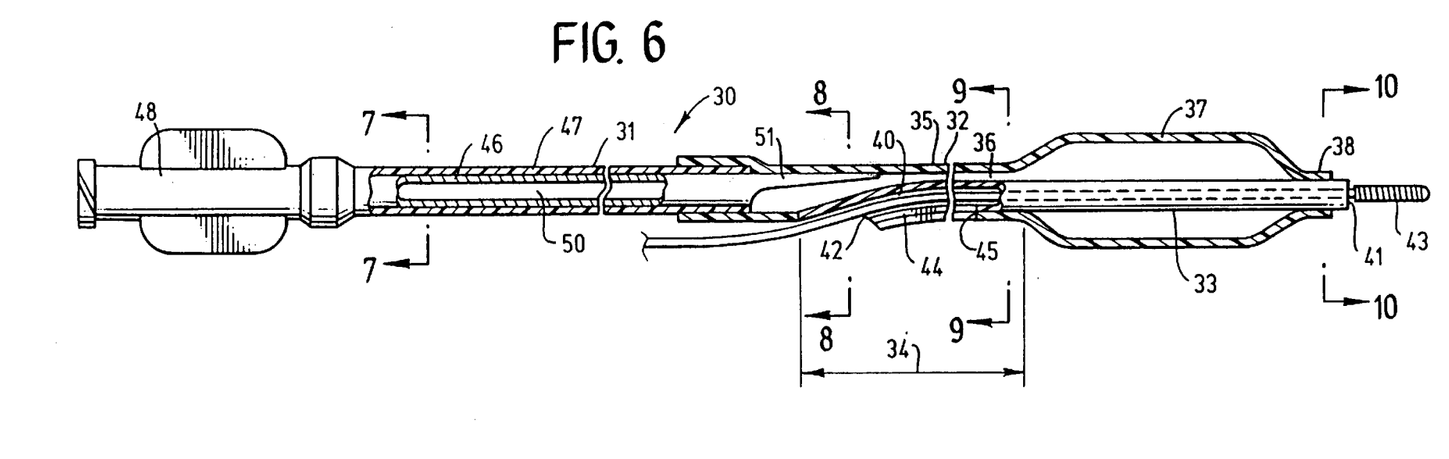
FIG. 6 is an elevational view, partially in section, of another dilatation catheter embodying features of the invention.
Figure 7:
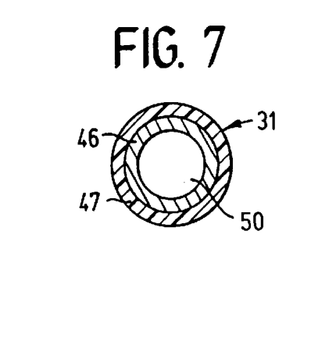
FIG. 7 is a transverse cross-sectional view of the catheter shown in FIG. 6 taken along the lines 7—7.
Figure 8:
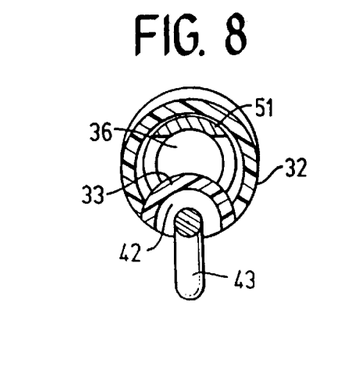
FIG. 8 is a transverse cross-sectional view of the catheter shown in FIG. 6 taken along the lines 8—8.
Figure 9:
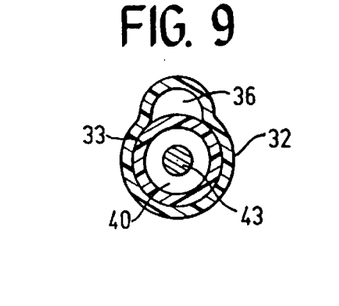
FIG. 9 is a transverse cross-sectional view of the catheter shown in FIG. 6 taken along the lines 9—9.
Figure 10:
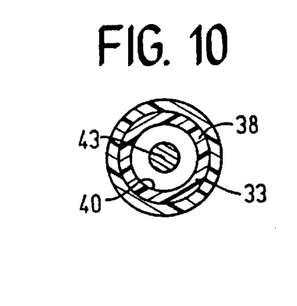
FIG. 10 is a transverse cross-sectional view of the catheter shown in FIG. 6 taken along the lines 10—10.
Figure 11:
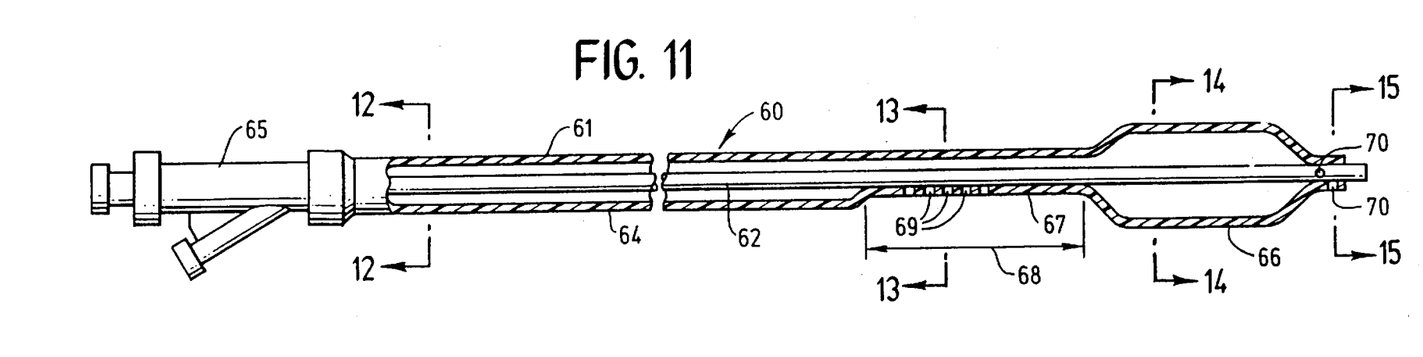
FIG. 11 is an elevational view, partially in section, of another dilatation catheter embodying features of the invention.
Figure 12:
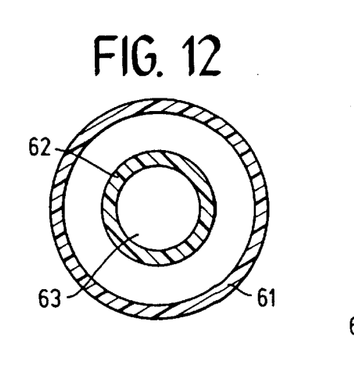
FIG. 12 is a transverse cross-sectional view of the catheter shown in FIG. 11 taken along the lines 12—12.
Figure 13:
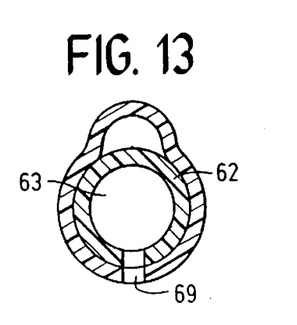
FIG. 13 is a transverse cross-sectional view of the catheter shown in FIG. 11 taken along the lines 13—13.
Figure 14:
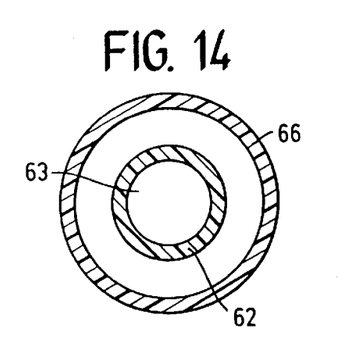
FIG. 14 is a transverse cross-sectional view of the catheter shown in FIG. 11 taken along the lines 14—14.
Figure 15:
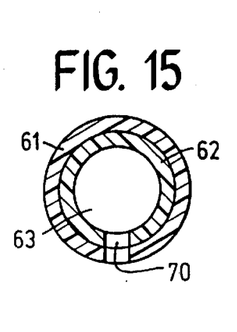
FIG. 15 is a transverse cross-sectional view of the catheter shown in FIG. 11 taken along the lines 15—15.

As shown in FIGS. 1 and 3, the distal portion of the outer tubular member 13 in part takes the shape of and is secured to the exterior of the inner tubular member 12 along the length 18. The unsecured portion 20 of the outer tubular member 13 along the length 18 forms with the inner tubular member 12 an inflation lumen 21 which is in fluid communication with the interior of the balloon 15. The inner lumen 22 of the inner tubular member 12 extends parallel to the inflation lumen 21 along the length 18. As best shown in FIG. 3, the transverse dimension of the catheter shaft 11 along the length 18 in the vertical direction is substantially larger than the transverse dimension of the catheter shaft in the horizontal direction along said length.

Figure 2:
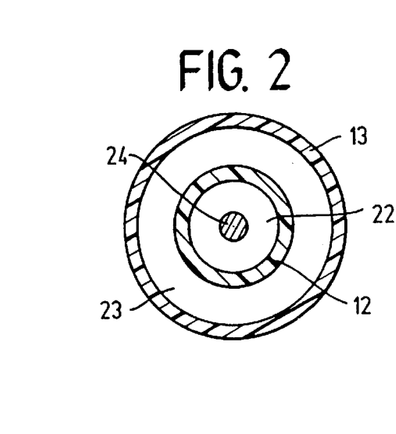
FIG. 2 is a transverse cross-sectional view of the catheter shown in FIG. 1 taken along the lines 2—2.

The proximal portion of the catheter shaft 11, as shown in FIGS. 1–3, is conventional where the outer tubular member 13 is disposed about but is unsecured to the inner tubular member 12 and defines with the inner tubular member an annular inflation lumen 23 which is in fluid communication with the inflation lumen 21 in the distal portion of the catheter shaft.

The use of the dilatation catheter shown in FIGS. 1–5 generally may follow conventional PTCA practices with over-the-wire type dilatation catheters. A guidewire 24 is backloaded into the inner lumen 22 of the inner tubular member 12 and both the guidewire and the catheter 10 are advanced together through a guiding catheter (not shown) which has been previously disposed within the patient's arterial system, with the distal end of the guiding catheter seated within the ostium of the desired coronary artery. The guidewire 24 is advanced out the distal end of the guiding catheter into the patient's coronary anatomy until it crosses the lesion to be dilated, and then the dilatation catheter 10 is advanced over the guidewire which is being herd in position, until the balloon 15 on the dilatation catheter is properly disposed within the stenotic region, so that the lesion can be dilated upon one or more inflations of the balloon. After the dilatation, the balloon 15 is deflated and the catheter 10 and the guidewire 24 may be withdrawn from the patient. If further treatment or diagnosis is to be conducted, the guidewire 24 can be replaced with an exchange wire before removing the dilatation catheter so that the first catheter can be removed and another advanced into the desired location or an extension wire can be attached to the proximal end of the guidewire in place which extends out of the patient to perform essentially the same function. See the discussion of exchange wires and extension wires in U.S. Pat. No. 4,827, 941 (Taylor et al.) which has been incorporated herein by reference.

FIGS. 6–10 schematically illustrate another dilatation catheter 30 embodying features of the invention which is configured for rapid exchange. The structure of the most distal portion of the catheter shaft 31 is quite similar to the embodiment shown in FIGS. 1–5 in that the distal section of the catheter shaft 31 includes an outer tubular member 32 which is disposed about an inner tubular member 33 and which in part takes the shape of and is secured to the exterior of the inner tubular member along a length 34 of the distal shaft. An unsecured portion 35 of the outer tubular member 32 forms an inflation lumen 36 which is in fluid communication with the relatively inelastic balloon 37. in this embodiment, the outer tubular member 32 and the balloon 37 are formed in a unitary construction. The distal skirt 38 of the balloon 37 is secured to the distal end of the inner tubular member 33.

Guidewire receiving inner lumen 40 extends proximally within the inner tubular member 33 from a distal guidewire port 41 in the distal end of the inner tubular member to a proximal guidewire port 42. A guidewire 43 is slidably disposed within the inner lumen 40 and extends out both the distal port 41 and the proximal port 42. A slit 44 is provided in the secured sections of the inner and outer tubular members 33 and 32 respectively and it extends distally from the proximal guidewire port 42 to a location 45 proximal to the balloon 37 to facilitate separation of the guidewire 43 and the catheter shaft 31 when replacing catheter 30 with another catheter as described in U.S. Pat. No. 4,748,982 (Horzewski et al.) which is incorporated herein by reference. The proximal guidewire port 42 is located at least about 5 cm but not more than about 45 cm from the distal end of the catheter.

The proximal portion of the catheter shaft 31 has a high strength inner tubular member 46, e.g. hypotubing, with a tightly fitting outer plastic jacket or coating 47. An adapter 48 is secured to the proximal end of the catheter shaft 31 to direct inflation fluid through the inner lumen 50 in the high strength tubular member 46 and the inflation lumen 36 between the inner tubular member 33 and the unsecured portion of the outer tubular member 32 to the interior of balloon 37. The distal extremity 51 of the high strength tubular member 46 is tapered to facilitate extension into the proximal end of the inflation lumen 36 where it is secured by suitable means such as an adhesive or by heat shrinking the proximal end of the outer tubular member about the tapered extremity 51. The high strength tubular member may be formed of stainless steel or a NiTi alloy, particularly a NiTi alloy with pseudoelastic properties, such as described in co-pending applications Ser. No. 07/629,381, filed Dec. 18, 1990; Ser. No. 07/994,679, filed Dec. 22, 1992 and Ser. No. 08/212,431, filed Mar. 11, 1994, assigned to the present assignee, Advanced Cardiovascular Systems, Inc. which are incorporated herein by reference. A dual lumen type construction such as described in Horzewski et al. above may also be used in the portion of the catheter shaft 31 proximal to the proximal guidewire port 42.

There are at least two modes of inserting the dilatation catheter 30 of this embodiment into the patient's coronary anatomy. The first method is for the most part the same as in the prior embodiment, namely, the guidewire 43 is preloaded into the short guidewire receiving inner lumen 40 of the inner tubular member 33 and both are advanced through a guiding catheter (not shown) previously disposed within the patient's arterial system with the distal end of the guiding catheter seated within the ostium of a coronary artery. The second mode, frequently called the "bare wire" technique, involves first advancing a guidewire 43 through and out the guiding catheter until the distal extremity of the guidewire is positioned within the patient's coronary artery across the lesion to be dilated. The proximal end of the guidewire 43, which is outside the patient, is backloaded, i.e. inserted into the short inner lumen 40 of the inner tubular member 33 and advanced proximally therein until it exits the guidewire port 42. The proximal end of the guidewire 43 is held in place and the catheter 30 is advanced over the guidewire through the patient's vascular system until the dilatation balloon 37 on the catheter is positioned across the stenotic region. The stenosis is dilated upon the inflation of the balloon 37, and, after the dilatation of the lesion, the balloon is deflated and the catheter is removed from the patient's artery. If other treatments are necessary, the catheter 30 is slidably withdrawn over the guidewire 43, leaving the guidewire in place so that other catheters can be advanced over the in-place guidewire in a similar manner without the need for exchange wires or guidewire extensions, thereby significantly reducing the overall time for the procedure.

FIGS. 11 through 15 illustrate yet another dilatation catheter 60 embodying features of the invention which provides for the perfusion of blood distal to the catheter during the dilatation of a stenotic lesion. The catheter 60 includes the catheter shaft 61, an inner tubular member 62 which has an inner lumen 63, an outer tubular member 64 disposed about the inner tubular member, an adapter 65 secured to the proximal ends of the inner and outer members, and a relatively inelastic balloon 66 which is secured by its distal end to the distal end of the inner tubular member 62. A portion of the outer tubular member 64 has a distal section 67 a length 68 of which is secured to the exterior of the inner tubular member 62 as previously described in the first two embodiments of the invention. The above-described portion of this embodiment has essentially the same structure as the embodiments shown in FIGS. 1–10.

The dilatation catheter shown in FIG. 11–15 differs from the other embodiments in that it has a plurality of perfusion ports 69 proximal to the balloon 66 which pass through the secured walls of the inner and outer tubular members 62 and 64 respectively and which are in fluid communication with the inner lumen 63 of the inner tubular member 62. Additionally, one or more perfusion ports 70 are provided distal to the balloon 66 through the wall of the inner tubular member 62 and are in fluid communication with the inner lumen 63 extending therein. In this manner, when the balloon 66 is inflated during an angioplasty procedure within a patient's vasculature, oxygenated blood is forced to pass through the proximal perfusion ports 69, through the inner lumen 62 and then out the distal perfusion ports 70 to provide oxygenated blood distal to the catheter 60 and thereby avoid the generation of ischemic conditions in downstream tissue. The transverse dimensions of the inner tubular member 62 within the secured section are preferably larger than in the embodiments previously discussed to allow for an increased flow of blood.

The use of the embodiment shown in FIGS. 11–15 is essentially the same as the embodiment shown in FIGS. 1–5. The only essential difference is that the balloon 66 can be inflated for significantly longer periods than the first described embodiments, e.g. typically about 20–30 minutes but possibly up to 5 hours or more, because oxygenated blood is continuously flowing to the tissue distal to the inflated balloon.

The dilatation catheter 30 shown in FIGS. 6–10 may be modified by providing a plurality of perfusion ports in the catheter shaft as shown in FIGS. 11–15 distal to the proximal guidewire port 42. However, the guidewire port 42 is preferably spaced sufficiently far proximally from the portion of the secured distal section having the perfusion ports so that the guidewire 43 can be pulled proximally and remain within the inner lumen 40 of the inner tubular member 33 while the balloon is inflated during a long term dilatation but not interfere with the flow of blood through the perfusion ports. After the angioplasty procedure is completed, the guidewire 43 can then be advanced distally through the inner lumen 40 and out the distal end thereof in order to maintain access to the lesion in case further treatment or diagnosis is necessary or desirable.

The above described catheters may be made by conventional techniques well known to those skilled in the art. Many suitable techniques are described in the references referred to herein. The small diameter distal sections may be formed by heat shrinking the portion of the outer tubular members which form the distal sections onto the underlying inner tubular members with a mandrel disposed in the space between the inner and outer tubular members so that upon the heat shrinking of the outer tubular member an inflation lumen is formed through the distal sections which is in fluid communication with the lumen in the proximal portion of the catheter body and the interior of the balloon. This bonds the small dimensioned distal section to the inner tubular member. A mandrel may also be inserted into the inner lumen of the inner tubular member to support the latter during the heat shrinking of the outer tubular member thereon to maintain its circularity. Alternate methods may be employed to make the small dimensioned distal section. For example, the small dimensioned distal section 17 may be preformed and then be adhesively bonded to the exterior of the inner tubular member. Multiple lumens similar to the inflation lumen may be formed in the small dimensioned section, such as the top and bottom thereof, by employing multiple mandrels when heat shrinking the outer tubular member onto the exterior of the inner tubular member.

Figure 16:
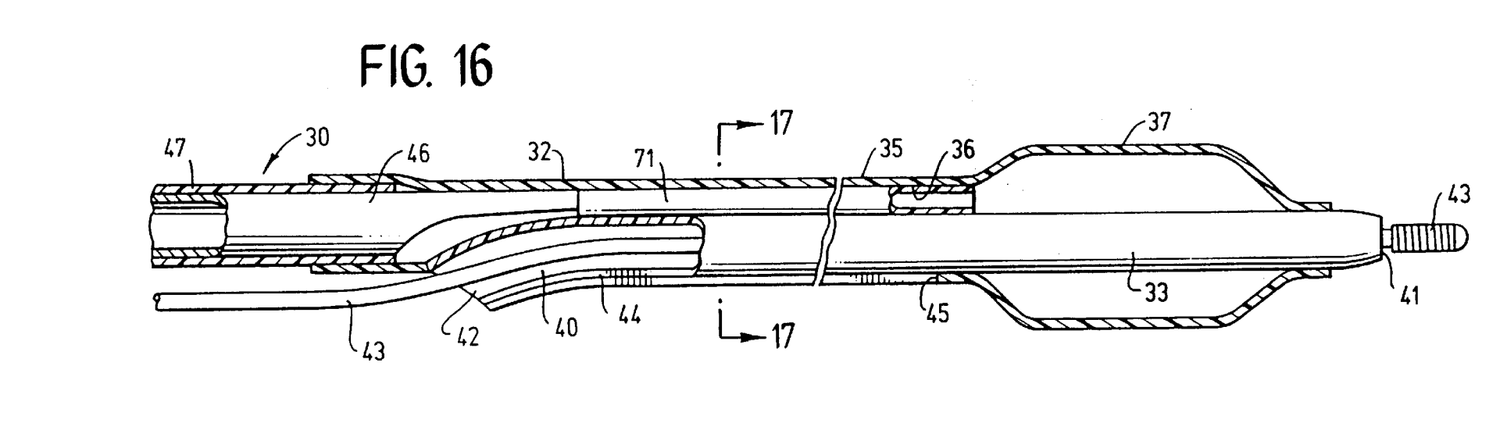
FIG. 16 is an elevational view, partially in section, of an alternative embodiment of the invention wherein a supporting tube is provided between the unsecured portion of the outer tubular member and the inner tubular member.
Figure 17:
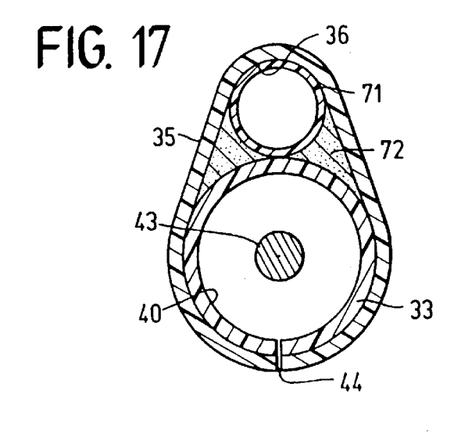
FIG. 17 is a cross-sectional view of the catheter shown in FIG. 16 taken along the lines 17—17.

With the embodiment of the invention shown in FIGS. 6–10 which have a slit 45 extending from the proximal guidewire port 42 through the secured portion of the catheter shaft 31 to facilitate the separation of the catheter and the guidewire, there is a tendency for the slit to open up when the fluid pressure within the inflation lumen 36 is raised to high levels to inflate the balloon 37 for dilatation of stenoses. The opening of the slit allows the guidewire to extend through the expanded or opened slit 44, but upon deflation of the balloon the slit closes onto the guidewire 43 which precludes independent movement of the guidewire and catheter. To avoid this problem, it is preferred to provide a support tube 71 to define the inner lumen 36 as shown in FIGS. 16 and 17 and to prevent the expansion of the unsecured portion of the outer tubular member 32. A filler 72 may be provided to eliminate voids between the support tube 71 and the unsecured portion of the outer tubular member 32. The support tube 71 may be formed of polyimide or other high strength polymer materials or metals such as the previously described pseudoelastic NiTi alloys. The catheter shown in FIGS. 16 and 17 is, except for the support tube 71 and filler 72, essentially the same as the catheter shown in FIGS. 6–10 and the corresponding parts are numbered the same.

Figure 18:
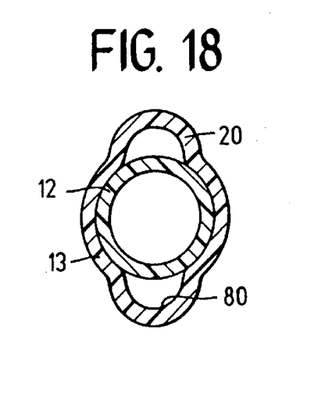
FIG. 18 is a cross-sectional view of a catheter shaft of another embodiment of invention wherein there are two unsecured lengths of the outer tubular which define lumens with the underlying inner tubular member.

FIG. 18 is an alternative distal shaft construction wherein an additional inner lumen 80 which can be used as an additional inflation lumen to vent air or to deliver other fluids. In this embodiment the additional lumen 80 should extend to the proximal end of the catheter shaft so that fluid can be introduced into or withdrawn from the additional lumen through an adapter mounted on the proximal end. For delivery or withdrawal of inflation fluid the lumen 80 should terminate within the interior of the inflatable dilatation member. The lumen 80 should extend to the distal end of the catheter to deliver fluids distal to the catheter.

Figure 19:
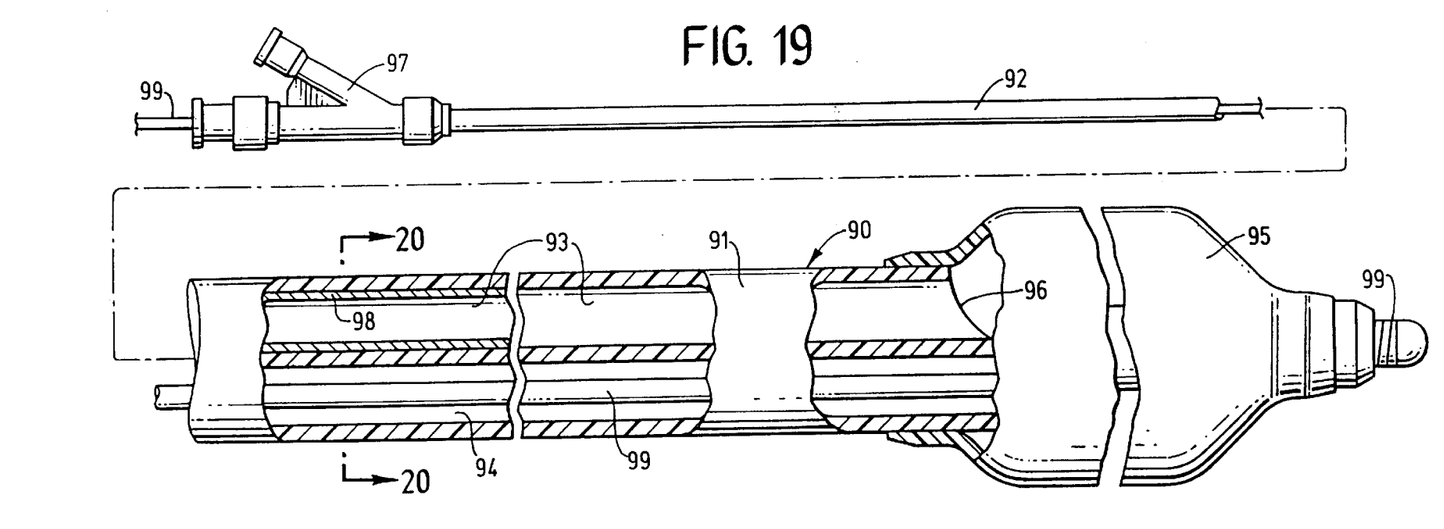
FIG. 19 is an elevational view, partially in section, of another embodiment of the invention in which the catheter shaft proximal to the balloon has the desired transverse cross-sectional dimensions and a hypotube formed of pseudoelastic NiTi alloy supports the inflation lumen to prevent kinking.
Figure 20:
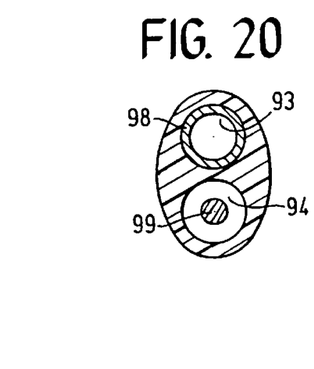
FIG. 20 is a transverse cross-sectional view of the embodiment shown in FIG. 19 taken along the fines 20—20.

FIGS. 19-20 illustrate an alternative embodiment of an over-the-wire dilatation catheter 90 which has a flexible distal shaft section 91, a stiffer proximal shaft section 92, an inflation lumen 93 and a guidewire receiving lumen 94. A dilation balloon 95 is mounted on the distal shaft section 91 having an interior which is in fluid communication with inflation lumen 93 through inflation port 96. The inflation lumen 93 extends from the adaptor 97 to the inflation port 96 through the proximal and distal shaft sections 92 and 91. An inflation lumen 93 and a guidewire receiving inner lumen 94 are stacked in the long direction of the transverse cross-sectional profile as shown in FIG. 20. The proximal shaft section 91 of the dilatation catheter 90 has a flexible hypotube 98 which defines the inflation lumen 93 as shown in FIG. 20 to prevent the kinking of the inflation lumen when the catheter is advanced through tortuous passageways. The hypotube 98 is preferably formed of an alloy, such as pseudoelastic NiTi alloy, having an austenite phase which is stable at body temperature and exhibiting a stressed induced austenite -to- martinsite phase transformation. The hypotube 98 extends at least the length of the proximal section of the catheter to a location proximal to the dilation balloon 95. Both proximal and distal shaft sections 92 and 91 have eliptical transverse cross-sections with the inflation lumen 93 and the guidewire receiving lumen 94 being stacked in the long direction of the transverse cross-sectional profile. The embodiment shown in FIGS. 19-20 depict an over-the-wire version of the catheter 90 with a guidewire 99 extending through the guidewire lumen 94 throughout its entire length.

Figure 21:
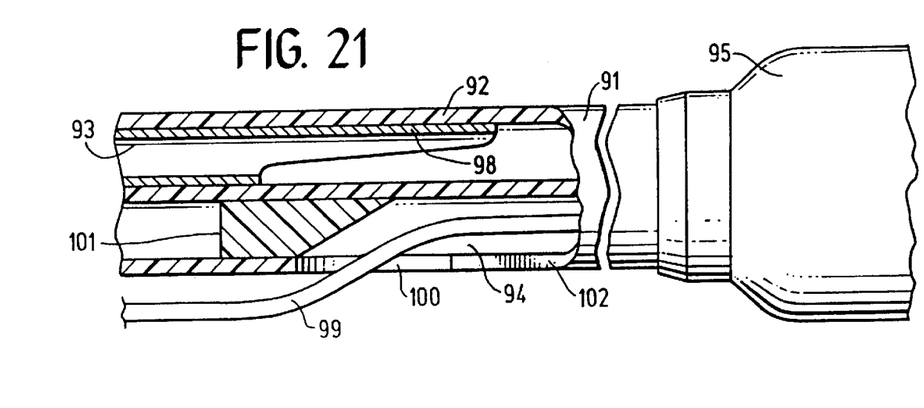
FIG. 21 is a partial elevational view, particularly in section, of a rapid exchange version of the catheter shaft shown in FIGS. 19-20.

FIG. 21 illustrates a modification of the catheter 90 shown in FIGS. 19-20 which is provided with a proximal guidewire port 100 in communication with the guidewire receiving lumen 94. A plug 101 may be provided in the guidewire receiving lumen 94 to urge the proximal end of guidewire 100 when the latter is advanced proximally through the guidewire lumen 94. If desired, the guidewire lumen 94 and the adaptor 97 may be provided with a slit 102 such as described in U.S. Pat. No. 4,748,982 (Horzewski) and U.S. Pat. No. 5,135,535 (Kramer) which are incorporated herein by reference.

Figure 22:
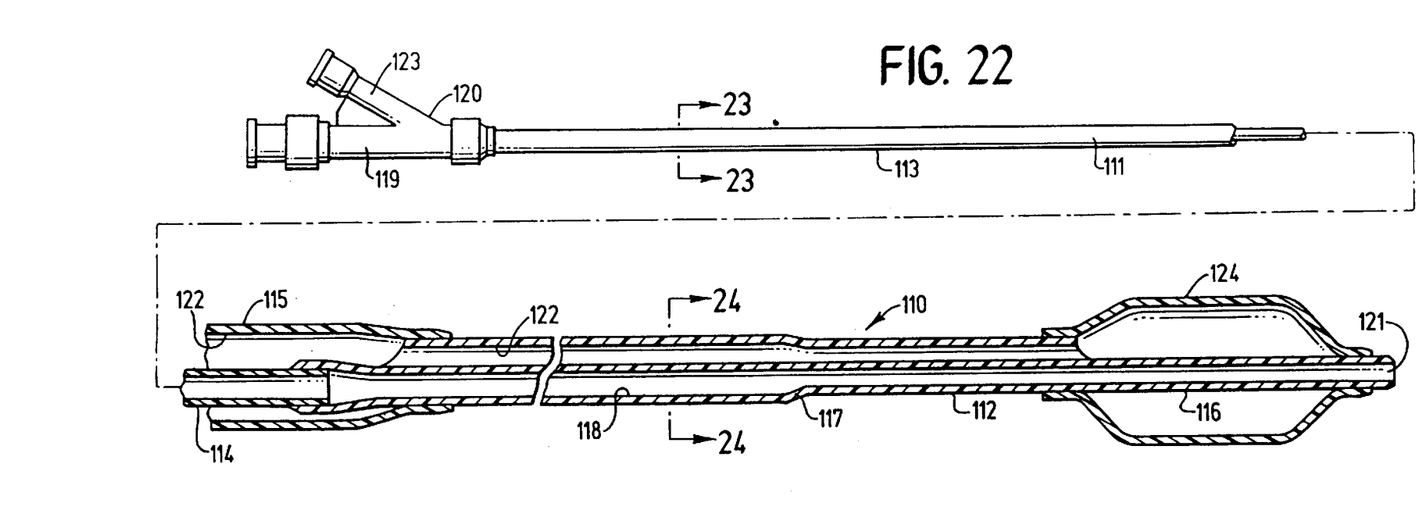
FIG. 22 is a elevational view, partially in section, of an alternative embodiment of an over-the-wire dilatation catheter.
Figure 23:
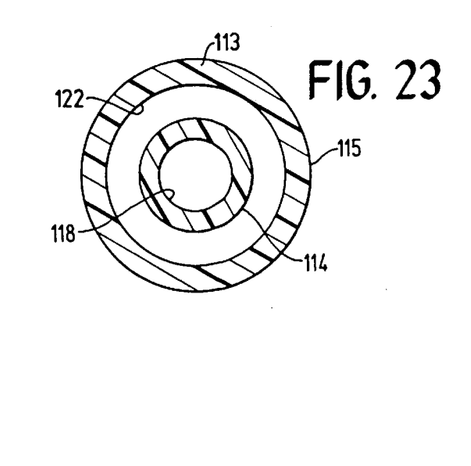
FIG. 23 is a transverse cross-sectional view of the embodiment shown in FIG. 22 taken along the lines 23—23.
Figure 24:
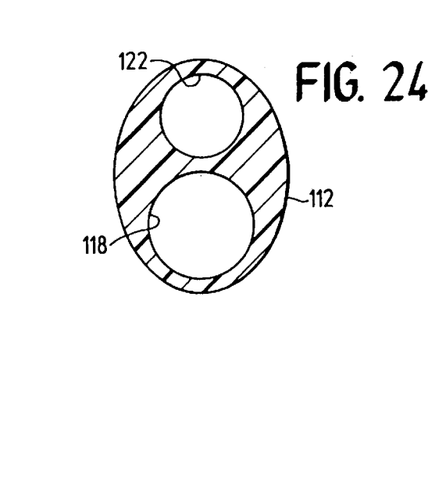
FIG. 24 is a traverse cross-sectional view of the embodiment shown in FIG. 22 taken along the lines of 24—24.

Another alternative embodiment of the invention is shown in FIGS. 22–24 wherein the dilatation catheter 110 has a catheter shaft 111 with a distal section 112 having an oblong transverse cross-sectional shape and a proximal section 113 having an inner tubular member 114 and an outer tubular member 115. The distal end of the outer tubular member 115 is secured about the exterior of the proximal end of the distal section 112 and the distal end of the inner tubular member 114 is secured to a cylindrical extension 116 of the distal shaft section 112. The distal shaft section 112 preferably tapers to smaller dimensions at location 117 to increase the flexibility of the distal most portion of the catheter shaft. A guidewire receiving inner lumen 118 extends within the inner tubular member 114 from the central arm 119 of the adapter 120 on the proximal end of the catheter shaft 111 through the distal section 112 to a guidewire port 121 in the distal end of the shaft. An inflation lumen 122 extends from the second arm 123 of adapter 120 through the annular space between the inner and outer tubular members 114 and 115, through the distal shaft section 112 into the interior of the inflatable member 124.

The various components of the catheters and guidewires of the invention can be formed from a wide variety of conventional materials. The catheter shaft, including the inner and outer tubular members may be made from polymeric materials such as polyethylene, polyamide, polyvinyl chloride, polyester (e.g. Hytrel® which is available from DuPont), polyetheretherketone (e.g. Grade 381G from Victrex U.S.A.) and other suitable polymeric materials. The hypotubing may be formed of stainless steel or NiTi super-elastic alloy material, such as described previously. The balloon may be made from polyethylene, polyethylene terephthalate and other relatively inelastic polymers and other materials.

The dimensions of the catheters generally follow the dimensions of conventional intravascular catheters. For coronary use the length is typically about 135 cm and the maximum outer diameter of the outer tubular member is about 0.02 to about 0.06 inch (0.51–1.52 mm). The transverse shape of the proximal section of the catheter shaft may be circular, oviform or elliptical.

While the invention has been described herein primarily in terms of certain preferred embodiments, the invention may be employed in a wide variety of embodiments. Additionally, modifications and improvements can be made to the invention without departing from the scope thereof.

Although individual features of embodiments of the invention may be shown in some of the drawings and not in others, those skilled in the art will recognize that individual features of one embodiment of the invention can be combined with any or all the features of another embodiment.

What is claimed is:

1. An elongated intraluminal catheter, comprising:

a) an elongated catheter shaft having proximal and distal ends, a first inner lumen configured to receive a guidewire and extending therein to a distal guidewire port in the distal end of the catheter shaft and a second inner lumen extending therein to a port spaced proximally of the distal end of the catheter shaft;

b) an inflatable member mounted on a distal portion of the catheter shaft proximal to the distal end of the catheter shaft for performing an intraluminal procedure, having an interior in fluid communication with the second inner lumen;

c) a flexible distal catheter shaft section which is proximal to the inflatable member, which has a length of at least about 4 cm and which has an oblong transverse shape with a first transverse dimension in a first direction substantially greater than a second transverse dimension in second direction perpendicular to the first direction; and d) tubular support member extending within at least a portion of the second inner lumen extending within the distal catheter shaft section, and having a lumen in fluid communication with the interior of the inflatable member on the distal portion of the catheter shaft.

2. The catheter of claim 1 wherein the first transverse dimension of the distal shaft section is at least 1.1 but not more than 3 times greater than the second transverse dimension.

3. The catheter of claim 1 wherein the first transverse dimension of the distal shaft section is at least about 1.2 to about 2.5 times greater than the second dimension.

4. The catheter of claim 1 wherein the first transverse dimension of the distal shaft section is at least 0.003 inch greater than the second transverse dimension.

5. The catheter of claim 1 wherein the first transverse dimension of the distal shaft section is at least 0.005 inch greater than the second transverse dimension.

6. The catheter of claim 1 wherein the catheter shaft proximal to the inflatable member for performing an intraluminal procedure has an elliptical or oviform transverse cross-sectional shape.

7. The catheter of claim 1 wherein the catheter shaft section having an oblong transverse shape is not more than about 40 cm in length.

8. The catheter of claim 1 wherein the proximal catheter shaft section has an oblong transverse cross-sectional shape.

9. The catheter of claim 1 wherein a proximal guidewire port is spaced a short distance proximally from the inflatable member and a substantial distance from the proximal end of the catheter and is in communication with the guidewire receiving first inner lumen.

10. The catheter of claim 9 wherein at least one perfusion port extends through a wall of the flexible distal shaft section proximal to the inflatable member and distal to the proximal guidewire port and is in fluid communication with the guidewire receiving first inner lumen.

11. The catheter of claim 1 wherein at least one perfusion port is provided in the flexible distal shaft section distal to the inflatable member which is in fluid communication with the guidewire receiving first inner lumen.

12. The catheter of claim 1 wherein the catheter has a proximal section formed at least in part of metal hypotubing having an inner lumen in fluid communication with the inflation lumen in the flexible distal section of the catheter shaft.

13. The catheter of claim 1 wherein the flexible distal catheter shaft section includes an inner tubular member having a passageway therethrough which defines the guidewire receiving first inner lumen, and an outer tubular member disposed about the inner tubular member and the inner tubular support member with at least about 30% but not more than about 90% of the inner periphery of the outer tubular member taking the shape of the exterior of the inner tubular member along a length thereof and with a portion of the inner periphery of the outer tubular member taking the shape of part of the exterior of the inner tubular support member.

14. The catheter of claim 13 wherein not more than 80% of the inner periphery of the outer tubular member along said length takes the shape of the exterior of the inner tubular member.

15. The catheter of claim 13 wherein a proximal guidewire port is provided through a wall of the flexible distal section which is spaced a short distance proximally from the inflatable member and a substantial distance from the proximal end of the catheter shaft and which is in fluid communication with the guidewire receiving inner lumen.

16. The catheter of claim 15 wherein at least one perfusion port extends through a wall of the flexible distal shaft section proximal to the inflatable member and distal to the proximal guidewire port where the outer tubular member takes the shape of and is secured to the inner tubular member and is in fluid communication with the guidewire receiving inner lumen.

17. The catheter of claim 15 wherein a slit extends distally from the proximal guidewire port through a portion of the catheter shaft in communication with the guidewire receiving inner lumen.

18. The catheter of claim 15 wherein the proximal guidewire port is spaced about 5 to about 40 cm from the distal end of the shaft.

19. The catheter of claim 15 wherein the proximal guidewire port is spaced about 10 to about 30 cm from the distal end of the shaft.

20. The catheter of claim 13 wherein the length of the outer tubular member which takes the shape of the inner tubular member is at least about 4 cm but not more than about 40 cm.

* * * * *